United States Patent [19]

Reischl et al.

[11] Patent Number: 5,369,003
[45] Date of Patent: Nov. 29, 1994

[54] PROCESS FOR THE SPECIFIC PRODUCTION OF RIBONUCLEIC ACIDS

[75] Inventors: Udo Reischl, Grafenau; Rudiger Rueger, Seeshaupt; Christoph Kessler, Dorfen; Rudolf Seibl, Penzberg, all of Germany

[73] Assignee: Boehringer Mannheim GmbH, Mannheim, Germany

[21] Appl. No.: 951,983

[22] Filed: Sep. 28, 1992

[30] Foreign Application Priority Data

Sep. 26, 1991 [DE] Germany .................. 4132133

[51] Int. Cl.⁵ .................................. C12Q 1/68
[52] U.S. Cl. .................. 435/6; 435/91.21; 435/91.3; 536/24.33
[58] Field of Search .......... 435/6, 91.21, 91.3; 536/24.33

[56] References Cited

FOREIGN PATENT DOCUMENTS 0200362 12/1986 European Pat. Off. .
0310229 4/1989 European Pat. Off. .
0320308 6/1989 European Pat. Off. .
0329822 8/1989 European Pat. Off. .
0373960 6/1990 European Pat. Off. .
0427073 5/1991 European Pat. Off. .
0427074 5/1991 European Pat. Off. .
WO88/10315 12/1988 WIPO .

OTHER PUBLICATIONS

Nucl. Acids Res. 15, 8783–8798 (1987).
Sengupta et al., *J. Biol. Chem.* 264(24), 14246–14253 (1989).

*Primary Examiner*—Margaret Parr
*Assistant Examiner*—Kenneth R. Horlick
*Attorney, Agent, or Firm*—Nikaido, Marmelstein, Murray & Oram

[57] ABSTRACT

Process for the production of ribonucleic acids or for the detection of template nucleic acids based on a transcription technique using two oligonucleotides which can hybridize to adjacent regions on the template nucleic acid without ligation of these oligonucleotides.

11 Claims, 7 Drawing Sheets

TEMPLATE-RNA : pspT18neo x EcoRI [POS. 1 : sp6 TRANSCRIPTION START]
ACCORDING TO BECK ET AL.

```
420   POS. 1933                           1958                                        1987
5'  GCUUGAUCCGGCUACCUGCCCAUUCGACCACCACCAAGCGAAACAUCGCAUCGAGGCGAGCACGUACUCGGAUGGAA  3'
              |_____|_____||_____|
                       P1                                   P2
              |_____||_____|
                         TEM 1                                 TEM 2
```

FIG.5

SEQUENCE LISTING ( 1 ) GENERAL INFORMATION:

( i i i ) NUMBER OF SEQUENCES: 14

( 2 ) INFORMATION FOR SEQ ID NO:1:

( i ) SEQUENCE CHARACTERISTICS:
      ( A ) LENGTH: 73 base pairs
      ( B ) TYPE: nucleic acid
      ( C ) STRANDEDNESS: single
      ( D ) TOPOLOGY: linear ( i i ) MOLECULE TYPE: RNA ( x i ) SEQUENCE DESCRIPTION: SEQ ID NO:1:

```
GCUUGAUCCG GCUACCUGCC CAUUCGACCA CCAAGCGAAA CAUCGCAUCG AGCGAGCACG      60
UACUCGGAUG GAA                                                         73
```

( 2 ) INFORMATION FOR SEQ ID NO:2:

( i ) SEQUENCE CHARACTERISTICS:
      ( A ) LENGTH: 51 base pairs
      ( B ) TYPE: nucleic acid
      ( C ) STRANDEDNESS: single
      ( D ) TOPOLOGY: linear ( i i ) MOLECULE TYPE: DNA ( x i ) SEQUENCE DESCRIPTION: SEQ ID NO:2:

```
GCTACCTGCC CATTCGACCA CCAAGCGAAA CATCGCATCG AGCGAGCACG T               51
```

( 2 ) INFORMATION FOR SEQ ID NO:3:

( i ) SEQUENCE CHARACTERISTICS:
      ( A ) LENGTH: 107 base pairs
      ( B ) TYPE: nucleic acid
      ( C ) STRANDEDNESS: single
      ( D ) TOPOLOGY: linear ( i i ) MOLECULE TYPE: DNA ( x i ) SEQUENCE DESCRIPTION: SEQ ID NO:3:

```
GAGTACGTGC TCGCTCGATG CGATGTTTCG CTTGGTGGTC GAATGGGCAG GTAGCTATAG      60
TGAGTCGTAT TAATTTTTAA AAAAAAAAT TAATACGACT CACTATA                    107
```

( 2 ) INFORMATION FOR SEQ ID NO:4:

( i ) SEQUENCE CHARACTERISTICS:
      ( A ) LENGTH: 108 base pairs
      ( B ) TYPE: nucleic acid
      ( C ) STRANDEDNESS: single
      ( D ) TOPOLOGY: linear ( i i ) MOLECULE TYPE: DNA ( x i ) SEQUENCE DESCRIPTION: SEQ ID NO:4:

```
GAGTACGTGC TCGCTCGATG CGATGTTTCG CTTGGTGGTC GAATGGGCAG GTAGCTATAG      60
TGAGTCGTAT TAATTTTTAA AAAAAAAAT TAATACGACT CACTATAG                   108
```

( 2 ) INFORMATION FOR SEQ ID NO:5:

( i ) SEQUENCE CHARACTERISTICS:
      ( A ) LENGTH: 29 base pairs
      ( B ) TYPE: nucleic acid
      ( C ) STRANDEDNESS: single
      ( D ) TOPOLOGY: linear ( i i ) MOLECULE TYPE: DNA ( x i ) SEQUENCE DESCRIPTION: SEQ ID NO:5:

```
GAGTACGTGC TCGCTCGATG CGATGTTTC                                        29
```

( 2 ) INFORMATION FOR SEQ ID NO:6:

( i ) SEQUENCE CHARACTERISTICS:

(A) LENGTH: 27 base pairs
(B) TYPE: nucleic acid
(C) STRANDEDNESS: single
(D) TOPOLOGY: linear (ii) MOLECULE TYPE: DNA (xi) SEQUENCE DESCRIPTION: SEQ ID NO:6:

GAGTACGTGC TCGCTCGATG CGATGTT 27

(2) INFORMATION FOR SEQ ID NO:7:

(i) SEQUENCE CHARACTERISTICS:
(A) LENGTH: 26 base pairs
(B) TYPE: nucleic acid
(C) STRANDEDNESS: single
(D) TOPOLOGY: linear (ii) MOLECULE TYPE: DNA (xi) SEQUENCE DESCRIPTION: SEQ ID NO:7:

GAGTACGTGC TCGCTCGATG CGATGT 26

(2) INFORMATION FOR SEQ ID NO:8:

(i) SEQUENCE CHARACTERISTICS:
(A) LENGTH: 25 base pairs
(B) TYPE: nucleic acid
(C) STRANDEDNESS: single
(D) TOPOLOGY: linear (ii) MOLECULE TYPE: DNA (xi) SEQUENCE DESCRIPTION: SEQ ID NO:8:

GAGTACGTGC TCGCTCGATG CGATG 25

(2) INFORMATION FOR SEQ ID NO:9:

(i) SEQUENCE CHARACTERISTICS:
(A) LENGTH: 30 base pairs
(B) TYPE: nucleic acid
(C) STRANDEDNESS: single
(D) TOPOLOGY: linear (ii) MOLECULE TYPE: DNA (xi) SEQUENCE DESCRIPTION: SEQ ID NO:9:

CGAGTACGTG CTCGCTCGAT GCGATGTTTC 30

(2) INFORMATION FOR SEQ ID NO:10:

(i) SEQUENCE CHARACTERISTICS:
(A) LENGTH: 30 base pairs
(B) TYPE: nucleic acid
(C) STRANDEDNESS: single
(D) TOPOLOGY: linear (ii) MOLECULE TYPE: DNA (xi) SEQUENCE DESCRIPTION: SEQ ID NO:10:

CCGAGTACGT GCTCGCTCGA TGCGATGTTT 30

(2) INFORMATION FOR SEQ ID NO:11:

(i) SEQUENCE CHARACTERISTICS:
(A) LENGTH: 30 base pairs
(B) TYPE: nucleic acid
(C) STRANDEDNESS: single
(D) TOPOLOGY: linear (ii) MOLECULE TYPE: DNA (x i) SEQUENCE DESCRIPTION: SEQ ID NO:11:

TCCGAGTACG TGCTCGCTCG ATGCGATGTT 30

(2) INFORMATION FOR SEQ ID NO:12:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (i i) MOLECULE TYPE: DNA (x i) SEQUENCE DESCRIPTION: SEQ ID NO:12:

ATCCGAGTAC GTGCTCGCTC GATGCGATGT 30

(2) INFORMATION FOR SEQ ID NO:13:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (i i) MOLECULE TYPE: DNA (x i) SEQUENCE DESCRIPTION: SEQ ID NO:13:

CATCCGAGTA CGTGCTCGCT CGATGCGATG 30

(2) INFORMATION FOR SEQ ID NO:14:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (i i) MOLECULE TYPE: DNA (x i) SEQUENCE DESCRIPTION: SEQ ID NO:14:

CCATCCGAGT ACGTGCTCGC TCGATGCGAT 30

PROCESS FOR THE SPECIFIC PRODUCTION OF RIBONUCLEIC ACIDS

The invention concerns a process for the specific production of ribonucleic acids and a process for the specific detection of nucleic acids as well as reagents for carrying out both these processes.

Nucleic acids acting as information carriers, are the basis for specific life forms for all organisms known up to now. They code for proteins; however, some nucleic acids probably also have catalytic or structural effects. Nucleic acids, because of their specificity, can also be used to differentiate between and to detect organisms. The individual nucleic acids are, however, only present in organisms in a very limited amount. It has therefore proven to be advantageous for the practical handling of nucleic acids to generate multiple copies of these nucleic acids in vivo (cloning) or in vitro (amplification). While the former method is time-consuming and complicated, the in vitro amplification has developed into a practical alternative in recent years.

A process is described in EP-A-200 362 which concerns an amplification of a part of a starting nucleic acid which proceeds in cycles. In each cycle an opposite strand is formed to each of the nucleic acids present. However, the reaction procedure results in a relatively large number of cycles.

In EP-A-0 320 308 a so-called ligase chain reaction is described. In this, oligonucleotides which are only separated in the hybridized state by a so-called nick are linked by a ligase reaction. The nucleic acid produced in this manner serves in turn as a template for ligation of the opposite strand oligonucleotides etc. This reaction has the same disadvantage as the PCR, namely that in each cycle the double-strands have to be separated again.

One attempts to circumvent this disadvantage in processes which are based on transcription steps which lead to a multitude of copies in isothermal cycles. Such a process is for example described in EP-A-0 310 229. In this process an oligonucleotide (promoter primer) which contains a template-specific region as well as a T7 promoter sequence is elongated on the template nucleic acid with mononucleotides. An opposite strand is then formed by means of a second primer. During this an opposite strand is also formed to the previously single-stranded promoter region and this therefore restores the functionality of the promoter. Afterwards a promoter-controlled transcription of the hybrid formed takes place. cDNA corresponding to the transcript RNAs formed is produced by means of an opposite strand primer. The hybrid is denatured and the cDNA is again reacted with promoter primer. Elongation of this primer on the cDNA again leads to a hybrid which contains a functional promoter. This molecule can also be introduced into the transcription cycle. A disadvantage of this reaction sequence is the fact that two elongation reactions are necessary to produce a transcribable molecule. The same problems also occur in the processes of WO 88/10315 and EP-A-0 329 822 as well as EP-A-0 373 960.

A process is proposed in EP-A-0 427 074 in which the template nucleic acid is reacted directly with a template-specific primer containing a promoter to directly form a transcribable molecule. The subsequent transcription yields RNA, one part of which corresponds to a part of the template nucleic acid and the other part of which is complementary to a further sequence located on the primer. A disadvantage of this process is that in the absence of template nucleic acid the reaction yields the same molecule as a by-product as that which is formed as the main product in the presence of the template nucleic acid. It is thus a relatively unspecific process. A process is also described in this patent application in which two different primers are used which are ligated on the template nucleic acid in the hybridized state whereby an elongated transcribable molecule is formed. A disadvantage is in this case the use of the ligase since it is an additional enzyme which usually requires other reaction conditions than the RNA polymerase with which the subsequent transcription takes place.

Another reaction for the synthesis of a transcribable nucleic acid is described in EP-A-0 427 073. In this process the 3' end of the template nucleic acid is ligated to the 5' end of a promoter primer. The template is bound to the promoter primer by hybridization with the template-specific sequence of the overhanging 3' end. This reaction therefore also requires an enzymatic reaction (ligase) for the production of the transcribable molecule. Moreover it has the disadvantage that only template nucleic acids with a defined 3' end can be detected.

The object of the present invention was therefore to provide a simple amplification process based on a transcription reaction which avoids the disadvantages of the state of the art. In particular it should yield a RNA product in a few steps and reduce the background signals which occurs in the transcription when promoter primers are used.

This object is achieved by the invention described in the following.

The invention concerns a process for the specific production of a multitude of ribonucleic acids using a template nucleic acid by
- direct hybridization of a template-specific promoter oligonucleotide P1 and of a further template-specific oligonucleotide P2 with the template nucleic acid T to form a complex K and
- promoter-controlled production of transcripts R which contain the template-specific sequence information from P1 and P2, in which the oligonucleotides P1 and P2 used are not enzymatically ligated together in any step in the process. A further subject matter is a process for the specific detection of nucleic acids which is based on the production process according to the present invention and reagents which are suitable for carrying out these processes.

In the process according to the present invention, the start of the reaction and to a certain extent the detection of the reaction products are a special embodiment of the so-called hybridization test, the essential features of which are known to one skilled in the area of nucleic acid diagnostics. To the extent that experimental details are not set forth in the following, reference is made in full detail to "*Nucleic acid hybridization*", published by B. D. Hames and S. J. Higgins, IRL Press, 1986, in particular in chapters 1 (Hybridization Strategy), 3 (Quantitative Analysis of solution hybridization) and 4 (Quantitative Filter Hybridization), Current Protocols in Molecular Biology, Edt. F. M. Ausubel et. al., J. Wiley and Son, 1987, in particular 2.9.1.–2.9.10 and Molecular Cloning, Edt. J. Sambrook et. al., CSH, 1989, in particular 9.4.7.–9.5.8. These in particular include the known methods for the production of labelled nucleoside triphosphates which are also described in EP-A-0 324 474, the chemical synthesis of modified and unmodified oligonucleotides, the cleavage of nucleic acids by means of restriction enzymes, the choice of hybridization conditions by which means a specificity can be achieved which is dependent on the extent of homology between the nucleic acids to be hybridized, their GC content and their length, as well as the formation of nucleic acids from deoxynucleoside triphosphates-or ribonucleotide triphosphates with the aid of polymerases, using so-called primers or promoter sequences.

A label within the sense of the present invention consists of a directly or indirectly detectable group L. Examples of directly detectable groups are radioactive ($^{32}P$), coloured or fluorescent groups or metal atoms. Indirectly detectable groups are for example immunologically or enzymatically active compounds such as antibodies, antigens, haptens or enzymes or enzymatically active parts of enzymes. These are detected in a subsequent reaction or reaction sequence. Haptens are particularly preferred since nucleoside triphosphates labelled with them can in general be used particularly well as substrates for polymerases and it is easy to carry out a subsequent reaction with a labelled antibody against the hapten or the haptenized nucleoside. Such nucleoside triphosphates are for example bromonucleoside triphosphates or digoxigenin-, digoxin- or fluorescein-coupled nucleoside triphosphates. The steroids mentioned in EP-A-0 324 474 and their detection have proven to be particularly suitable. With regard to their incorporation into nucleic acids reference is hereby made to EP-A-0 324 474.

A specific production process or test is understood as a process by which means certain nucleic acids can be produced or detected selectively, if desired, also in the presence of other nucleic acids. It is, however, also possible to make the object of the process the production or detection of several nucleic acids or a group of nucleic acids with a partially corresponding or similar nucleotide sequence, or several sections of a nucleic acid in the presence of other nucleic acids. Either of the two complementary strands can be used for the detection of double-stranded nucleic acids. An essentially complementary nucleic acid or nucleic acid sequence is understood as nucleic acids or sequences which can hybridize with the corresponding nucleic acid and have a nucleotide sequence in the hybridizing region which is either exactly complementary to the other nucleic acid or differs by only a few bases from the exactly complementary nucleic acid. In this case the specificity depends on the degree of complementarity as well as on the hybridization conditions. Oligonucleotides which are essentially complementary to a part of a template nucleic acid are denoted template-specific in the following.

The basis of the process according to the present invention are samples which contain nucleic acids which are purified or combined with other components, in particular with other nucleic acids. The sample can contain further constituents such as proteins, salts etc. Using the process according to the present invention it is possible to amplify nucleic acid sequences if these sequences are present in a nucleic acid present in the sample. The nucleic acid which is intended to form the basis for the production of ribonucleic acids is denoted template nucleic acid (or template) in the following.

Nucleic acids can be produced with the process according to the present invention which contain the entire nucleotide sequence information of the template nucleic acid but preferably contain only parts thereof. In order to amplify partial sequences of the template nucleic acid it is not necessary, but possible, to fragment the template nucleic acid before carrying out the process.

In order to carry out the process the template nucleic acid must be present as a single strand. This is normally the case for RNA without further pretreatment. In the case of DNA a double-stranded template nucleic acid can be made single-stranded by denaturation in a simple known manner.

A promoter oligonucleotide within the sense of the invention is a nucleic acid which contains a double-stranded region PRO which starts the synthesis of RNA by recognizing and binding RNA polymerase. This PRO region contains a sequence which initiates the transcription of the nucleic acid region adjoining this sequence in the downstream direction by a RNA polymerase. The double-stranded PRO sequence preferably has a length of 17-100 bases, particularly preferably 17-50 bases. Suitable double-stranded sequences which can bind a RNA polymerase are described for example in Nucleic Acids Research 12, pages 7035-7056 (1984) and in Protein Sequences and DNA Analysis 1, pages 269-280 (1988), Biophysical Chemistry, Part III, p. 1183-1211, Freeman & Co., San Francisco, 1980; J. Bacteriol 170, p. 5248-5256 (1988); Biochem. J. 224, p. 799-815 (1984); Gene Acal. Techn. 6, p. 29-32 (1989), EP-A-0 292 802 and Nucleic acid probes, ed. Symons (CRC Press, Boca Raton, 1989). The two strands of the double-stranded portion can either be present in an open form or can be linked upstream in the form of a hairpin structure. The hairpin region (also denoted loop) linking the complementary single strands is preferably 5—50 nucleotides and particularly preferably 5-10 nucleotides long, and is preferably composed of only one type of nucleotide. The promoter oligonucleotide P1 has a single-stranded template-specific region TEM1' at the downstream 5' end. The TEM1' region is preferably 6 to 50 nt, particularly preferably 12 to 30 nt long.

The double-stranded promoter region PRO can be separated from the template-specific sequence TEM1' by a sequence of further nucleotides.

The 3' end of the promoter oligonucleotide P1 is preferably non-phosphorylated while the 5' end can be phosphorylated or non-phosphorylated. The downstream 3' end of P1 can also be blocked against elongation e.g. by a dideoxynucleotide. The promoter oligonucleotide P1 can in addition contain a further single- or double-stranded nucleotide sequence in the downstream region adjoining the sequence PRO. Sequences which promote transcription are preferred (Nucl. Acids Res. 15, p. 8783-8798 (1987)). The region of the primer 1 which contains the additional self-complementary but not template-complementary, transcribable sequences which promote transcription as described by J. F. Milligan et. al. (1987), Nucl. Acids Res., 15, p. 8783-8798 can be 1-20 nucleotides long; it is preferably 5 nucleotides (CCGCG) long. There can, however, also be additional nucleotide sequences between PRO and TEM1' which enable further reaction steps (start sequences for replication (ori sequences), restriction cleavage sites, replicable sequences, binding sites for sequencing primers, protein binding site).

The region between transcription start and TEM1' can be 0-150 nt long. The template-specific oligonucleotide P2 contains a nucleotide sequence TEM2' which is essentially complementary to a further nucleotide sequence of the template nucleic acid and can therefore hybridize with this sequence. This sequence is preferably 6 to 50 nt long, particularly preferably 12 to 30 nt long. The specificity of the production process according to the present invention can be controlled by its length and complementarity. For example by suitable choice of this sequence it is possible to specifically make only one of several template nucleic acids (e.g. nucleic acids of various bacterial genera or bacterial species in mixtures) in the sample the object of the process according to the present invention and to amplify their sequence.

In a first step of the process according to the present invention for the specific production of nucleic acids, the sample, which contains the template nucleic acid, is reacted with the promoter reagent P1 and the template-specific oligonucleotide P2 under hybridization conditions. In this process a transcribable nucleic acid complex K is formed in which the template nucleic acid is hybridized to the oligonucleotide P1 via a double-stranded region TEM 1/TEM 1' and to the oligonucleotide P2 via a double-stranded region TEM 2/TEM 2'. In the downstream direction further oligonucleotides P3 . . . PN can be hybridized to the template nucleic acid via further regions TEM 3 . . . TEM N. The TEM 1 region is different from the TEM 2 region of the nucleic acid. The regions TEM 1' and TEM 2' are preferably directly adjacent on the template nucleic acid so that they are only separated by a nick. In the hybridized state the 5' end of the oligonucleotide P1 and the 3' end of the primer P2 are preferably directly adjacent to one another or separated by 1-10, preferably by 1-5 nucleotides but are, however, not covalently linked to one another. They can, however, also be separated by 1-150, preferably 1-1000 nt. This gap is then preferably firstly filled up by a gap filling reaction (DNA polymerase or reverse transcriptase, dNTPs) so that a nick remains. The primer P2 or the primer PN which binds in the downstream region can contain further nucleotides in its 5' region in addition to the sequence TEM 2' or TEM N' which do not hybridize to the template nucleic acid. Such a sequence could for example be an ori sequence (start region for a replication), a replicable sequence, a RE site, a sequence for binding a nucleic acid binding protein, a homopolymeric sequence or a further promoter sequence. P2 . . . PN preferably has an OH group at its 5' and 3' end. Each of the hybridization regions TEM 1 and TEM 2 are preferably 6-50 nt and particularly preferably 12-30 nt long.

An essential feature and advantage of the invention is that in contrast to the known processes oligonucleotides P1 and P2 are not enzymatically linked (ligation) after the hybridization reaction of T, P1 and P2. This obviates the adjustment of the reaction conditions for the ligase reaction and in particular the use of a ligation enzyme. However, a prerequisite is that a transcriptase is used in the subsequent transcription reaction which, regardless whether the "opposite strand" (of P1, P2, P3 . . . PN) of the template nucleic acid has one or several nicks or gaps, forms a transcript over the entire length of the double strand from the transcription starting point of the promoter to the 5' end of the oligonucleotide P2 or, if desired, of the oligonucleotide PN. A person skilled in the art can find a suitable transcriptase in a simple manner. An appropriate experiment is described in example 3. One of the enzymes which is suitable for the process according to the present invention is T7 RNA polymerase.

After formation of the nucleic acid complex K it is subjected to a promoter-controlled enzymatic transcription. The reaction conditions under which a promoter-controlled transcription can proceed are the same for this complex as for the transcription reactions of the state of the art. They depend on the chosen promoter/polymerase system. Examples of promoter systems are known from the phages T7, SP6 and T3. Basically a RNA polymerase and ribonucleoside triphosphates (NTPs) are required. The transcription system of T7 (T7 RNA polymerase and T7 promoter) has proven to be a particularly preferred transcription system. The polymerases used can also be thermostable.

The T7 RNA polymerase-promoter-specific complementary sequence regions within the double-stranded region of the promoter oligonucleotide P1 can be between 12 and 20 nucleotides long (shortest and longest functional promoter sequence which is described by Milligan et. al. (1987), Nucl. Acids Res., 15, p. 8783-8798). The double-stranded region has preferably a length of 17 nucleotides.

Products of the transcription are RNA transcripts R whose 5' ends are defined by the transcription starting point and whose 3' ends by the 5' terminal position of the TEM 2 region. When further oligonucleotides P3 . . . PN are used the transcripts preferably end with a ribonucleotide complementary to the 5' terminal position of the furthest oligonucleotide. This RNA in particular contains the sequences which are homologous to TEM 1 and TEM 2.

In the case of a hybridization of primer 1 alone a shorter transcript is formed independent of the binding to the template which extends to the 5' end of primer 1.

The transcript R which forms can be the final product of the process according to the present invention for the production of ribonucleic acids. However, this transcript is preferably further amplified in a cyclical reaction process.

Since the transcripts R are homologous to T and contain the sequence informations of TEM 1 and TEM 2 they can preferably in turn be template nucleic acids for the formation of a transcribable complex K' from R, P1 and P2 which can then again be transcribed. Thus an amplification can be achieved by using the transcripts again and again in the reaction sequence
formation of K'
transcription.

A great advantage of this procedure is that a ligase does not have to be used in any phase.

An advantage over processes in which the transcripts have to be firstly transcribed into cDNA and these then have to be converted with a promoter primer into a transcribable complex which is then transcribed is that the formation of cDNA can be omitted; this saves the use of a further enzyme.

Thus according to the present invention ribonucleic acids can in principle be formed from a single-stranded template nucleic acid using only a single enzyme (a promoter-controlled polymerase) without denaturing steps between the enzymatic reaction steps. Temperature cycles or cyclical changes in the reaction conditions are not necessary. The number of reaction steps is very small.

The aforementioned cycle can be continued until the desired number of nucleic acids is formed.

The ribonucleic acids formed can be purified or/and processed further in a known manner. For example cDNA can be produced from the transcripts R e.g. by using the primers P2 . . . PN.

In order to test whether an adequate number of nucleic acids has been formed, a detectably labelled detector probe is for example added which can hybridize with the desired product and the hybrid is detected or the nucleic acids formed can be directly detected by incorporation of detectably labelled mononucleotides.

An advantage of the process according to the present invention is that it can proceed isothermally i.e. it can be carried out at one temperature.

Moreover it is a template-specific amplification and not only a signal amplification. Only one set of mononucleotides is necessary (ribonucleotides). This means lower production costs and no mutual inhibition of the polymerases. The oligonucleotides are easy to produce and do not need to have their 3′ ends blocked since no DNA polymerase is present. In the process according to the present invention defined ends for the template nucleic acid are not necessary and therefore corresponding prereaction steps can be omitted. The disadvantage of the LCR or repair chain reaction that the opposite strand oligonucleotides cross-react with the specific oligonucleotides does not apply since opposite strand oligonucleotides are not necessary. Nevertheless the reaction is essentially exponential since each of the transcripts in turn can act as a template.

In an embodiment of the process according to the present invention in order to stabilize the single strand configuration in the region of the sequences TEM1 and TEM2 of the template nucleic acid, blocking oligonucleotides BLO1 and BLO2 are hybridized in the regions BLO1′ and BLO2′ which are adjacent to TEM1 and TEM2. The BLO1′ region is preferably located 2–10 nucleotides upstream of TEM1. The BLO2′ region should be more than 10 nucleotides downstream of the binding site TEM2. The oligonucleotides BLO1 and BLO2 preferably contain a modification to block polymerase activity at the 3′ end, in order to prevent elongation, for example by dideoxyribonucleotides. The use of further blocking oligonucleotides is possible.

In a further embodiment TEM2 is at a distance of 1–150, preferably of 1–1000 nt from the 5′ end of the TEM1 region (a in FIG. 4). This gap between P1 and P2 can be filled up with a RNA-dependent or DNA-dependent DNA polymerase and dNTP in the reaction mixture. In this case 3′-blocked oligonucleotides P1 are preferably used.

If this "gap" consists of 1–10 nucleotides and particularly preferably of 1–5 nucleotides (primers P3–P6 and primers P7–P11 in FIG. 7) then this can be read through by the T7 RNA polymerase without a prior gap-filling reaction. The length of the transcript which is produced in this process corresponds to the sum of the length of the transcribable sequence of primer 1 and the length of the primer 2 used.

Thus in a further preferred embodiment the sequence of primer 2 is chosen so that after hybridization to the template there is a "gap" (see above) of 1–10, particularly preferably of 1–5 nucleotides, between the 5′ end of primer 1 and the 3′ end of primer 2. In the absence of DNA polymerase activity this gap can be read through by the RNA polymerase during the transcription i.e. the nucleotide complementary to the 5′ end of primer 1 and the nucleotide complementary to the 3′ end of primer 2 are directly adjacent in the transcript which is produced. The sequence of the transcript then only contains the nucleotides which correspond to the transcribable region of the template that is present in a double-stranded form in K.

Hybridization of several different primers to a template starting at promoter oligonucleotide 1 in the direction of transcription enables a universal gene synthesis with concomitant introduction of mutations by gaps between the individual primers.

The invention therefore also concerns a process for the production of deletion-mutant nucleic acids using a template nucleic acid which comprises the following steps:

Hybridization of at least one promoter primer and one oligonucleotide which each have a template-specific region whereby these template-specific regions are essentially complementary to regions of the template nucleic acid which are located 1–10 nucleotides apart on the template nucleic acid and promoter-controlled transcription.

This process utilizes the property of RNA polymerases, in particular of T7 RNA polymerase to read through in this connection a deletion-mutant nucleic acid is understood as a nucleic acid which is essentially complementary to a particular template nucleic acid but which, however, differs from a complete transcript in that one or several nucleotides are missing. The missing region is not one which is located directly at the 3′ or 5′ end of the complete transcript.

The deletion-mutant ribonucleic acids which are formed first according to the present invention can be subject to further reactions in a known manner (cDNA formation or renewed reaction with P1 and P2 which can then hybridize with the nucleic acid without a gap).

The present invention in addition concerns a process for the specific detection of nucleic acids which includes the process according to the present invention for the specific production of nucleic acids and its embodiments in which the transcripts R or their secondary products are detected. In this connection secondary products are in particular understood as cDNA which may be formed subsequently. The detection of these products can in principle be carried out in a known manner for example by hybridization with labelled probe nucleic acids and detection of labelled hybrids. Another simple method is the incorporation of labelled mononucleotides during the transcription reaction or/and the separation of the reaction products by gel electrophoresis.

A particularly preferred embodiment of the process according to the present invention utilizes the incorporation of a detectably-labelled monoribonucleotide during the transcription reactions and hybridization with a capture probe which is either bound directly to a solid phase or is preferably made immobilizable by coupling to a chemical group such as e.g. biotin. In the case of immobilizable probes it is possible to subsequently immobilize on a solid phase which has a binding affinity to the chemical group. The label on the solid phase is preferably detected after separating the detectably-labelled mononucleotide. Digoxigenin-UTP (EP-A-0 324 744) or fluorescein-UTP is preferably used as the detectable group. The presence of this group on the solid phase is then detected by means of an enzyme-labelled antibody against digoxigenin.

Sequences are preferably selected for the capture or detection probe which are homologous to partial sequences or to the whole sequence of P2 (or if desired PN) or are homologous to the 5' region of P1 and 3' region of P2 (in each case ca. 10 nt). They are preferably 6–5000 nt and particularly preferably 12–50 nt long. In the filling up reaction they are preferably located in the region between P1 and P2 (filling up region); this results in a further advantage for the specificity of the detection.

In a further embodiment P2 is labelled with a group capable of immobilization which is preferably at the 5' end. The complexes K and K' can be bound via this group to a solid phase in order to isolate them from mixtures.

In addition immobilizable P2 can be hybridized to the transcript R and in this way incorporated detectably-labelled mononucleotides can for example be detected by detection during the transcription. An advantage of this procedure is that no further capture probe is necessary since P2 can serve as such.

In a further embodiment P1 is immobilizably-modified. Then the transcription complex K can for example be bound to a solid phase and thus be separated from a mixture of nucleic acids.

The detection method according to the present invention has all the advantages of the process for the production of nucleic acids according to the present invention.

Examples of detection methods are shown in each of the figures. However, these are also production processes according to the present invention when the detection steps are omitted.

The invention also concerns reagents and reagent kits for carrying out the processes according to the present invention.

The invention therefore concerns a reagent which contains the following components:
 a template-specific promoter oligonucleotide P1 which contains a template-specific sequence TEM1 in addition to the double-stranded promoter sequence PRO and
 at least one template-specific oligonucleotide P2.

The reagent in addition preferably contains at least one of the aforementioned oligonucleotides BLO1 and BLO2 or others. It also preferably contains the four types of mononucleoside triphosphates which are either unmodified or detectably or immobilizably modified. Furthermore it can contain pH buffers and auxiliary substances e.g. stabilizers, in particular those substances which are suitable for the transcription reaction. However, it contains no ligase.

In addition the invention concerns a reagent kit which contains in separate containers:
1) the promoter oligonucleotide P1 and the template specific oligonucleotide P2 and monoribonucleoside triphosphates; and
2) a suitable transcription enzyme for the promoter
3) no ligase The reagent kit can also contain the constituents stated in 1) separated from one another.

In addition the reagent kit can contain control nucleic acids and/or reagents for preparing the samples.

If the reagent kit is to be used for the detection of nucleic acids or nucleotide sequences it preferably contains the reagents which are necessary for this in a separate container e.g. capture or/and detection probes.

Figure 1:
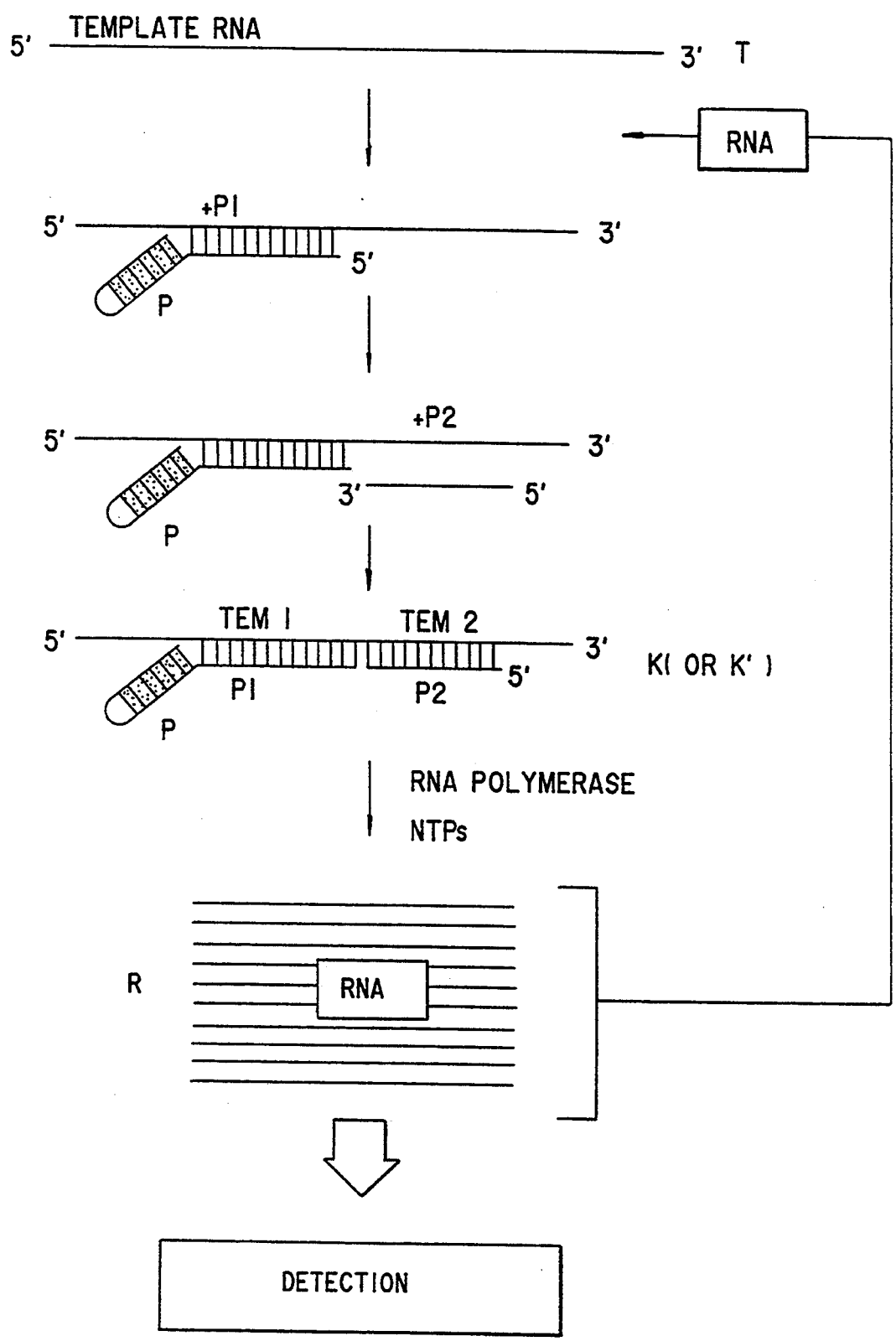
FIG. 1 shows a diagram of the detection method according to the present invention. The oligonucleotides P1 and P2 can be added separately or together. Their amount and concentration are preferably the same. If sufficient P1 and P2 were added at the beginning then a subsequent addition of P1 and P2 is not necessary. The same applies to the other reagents, in particular to the enzyme and the mononucleotides.
Figure 2:
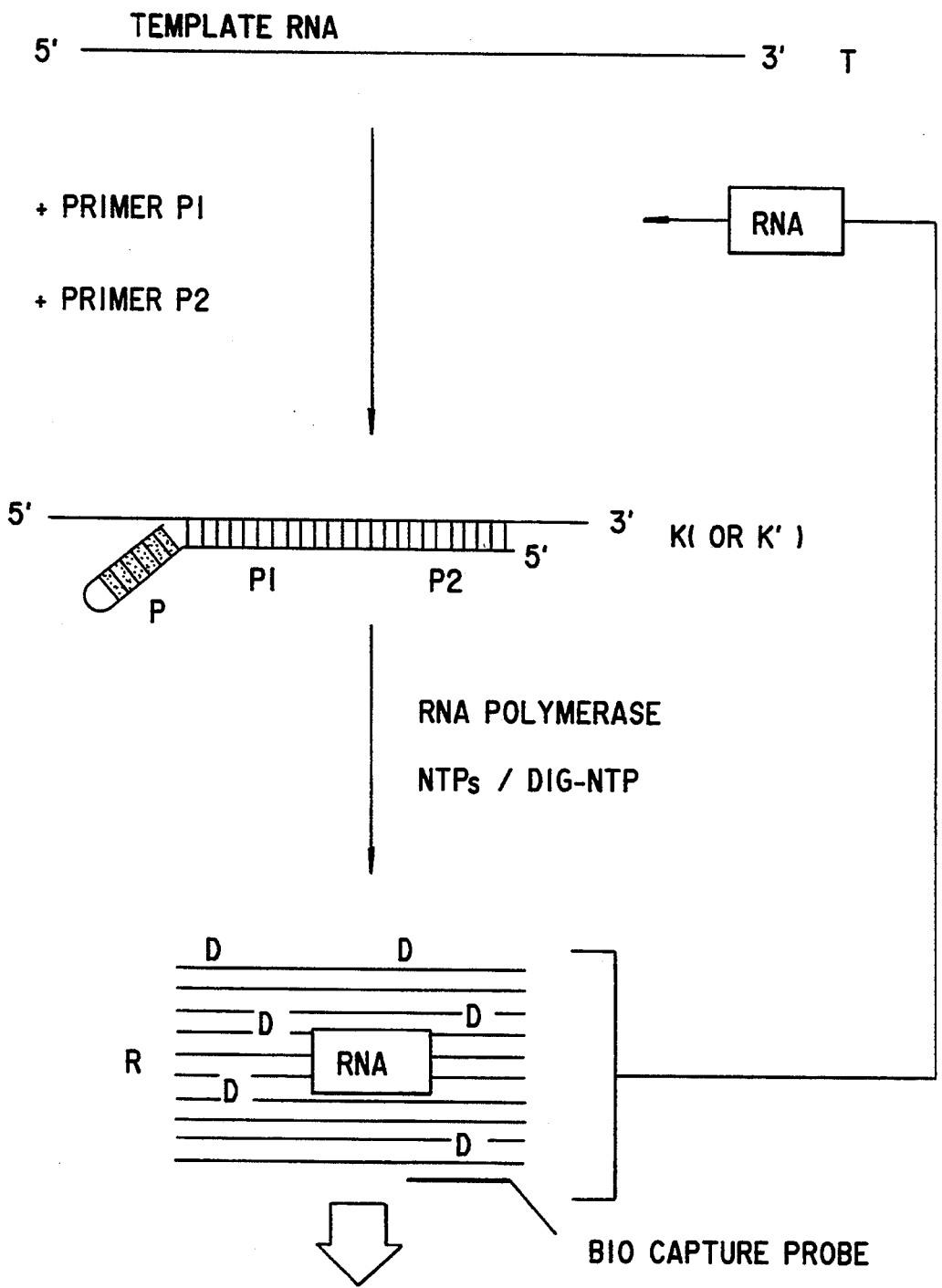
FIG. 2 shows an embodiment of the method of detection according to the present invention in which detectably labelled monoribonucleoside triphosphates are incorporated and subsequently the transcripts are trapped by means of a biotinylated capture probe.
Figure 3:
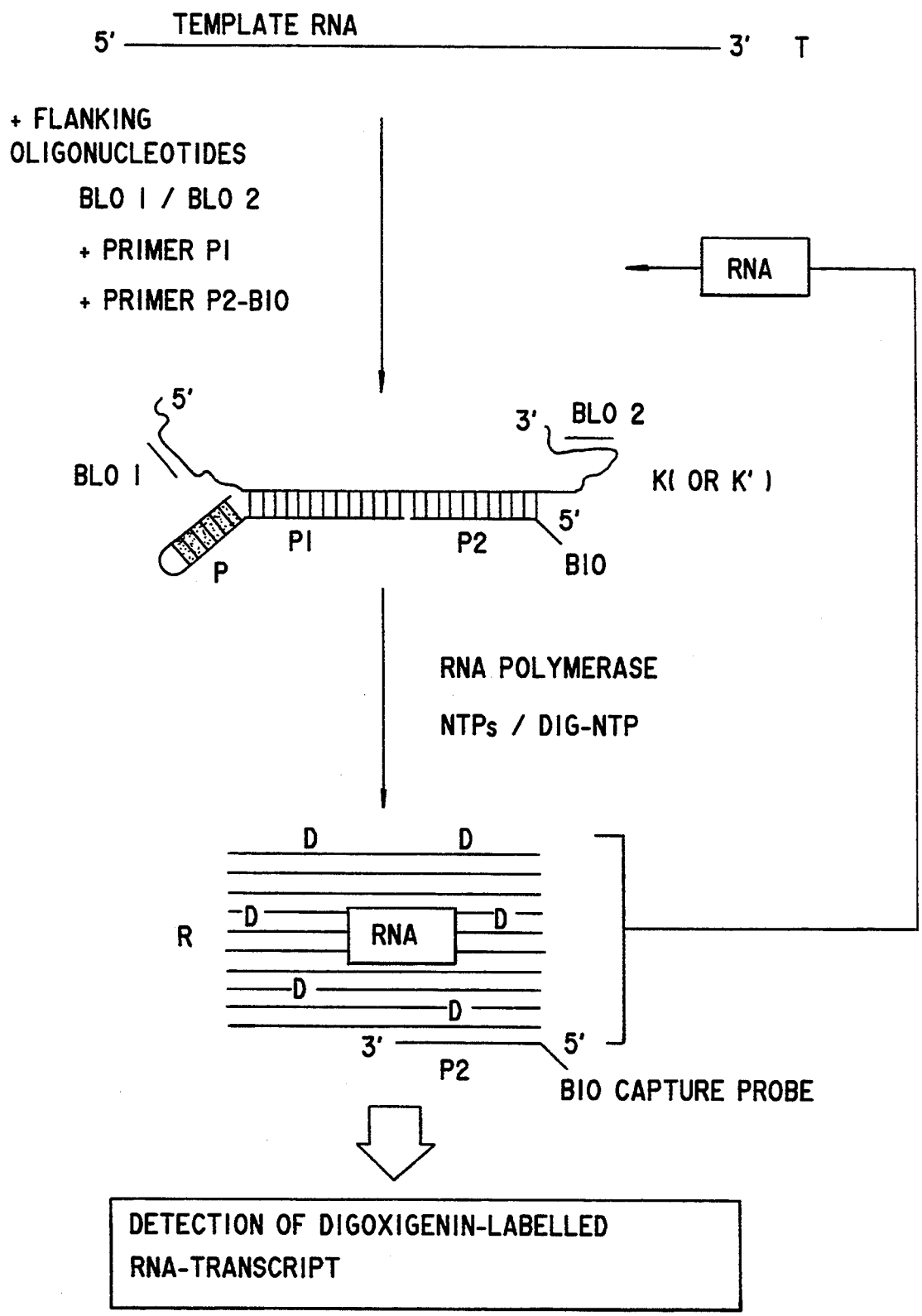
FIG. 3 shows an embodiment in which protecting oligonucleotides BLO1 and BLO2 as well as an immobilizable, substituted oligonucleotide P2 are used. In this embodiment a hybrid of P2 and R is detected, which is detectable as well as immobilizably labelled.
Figure 4:
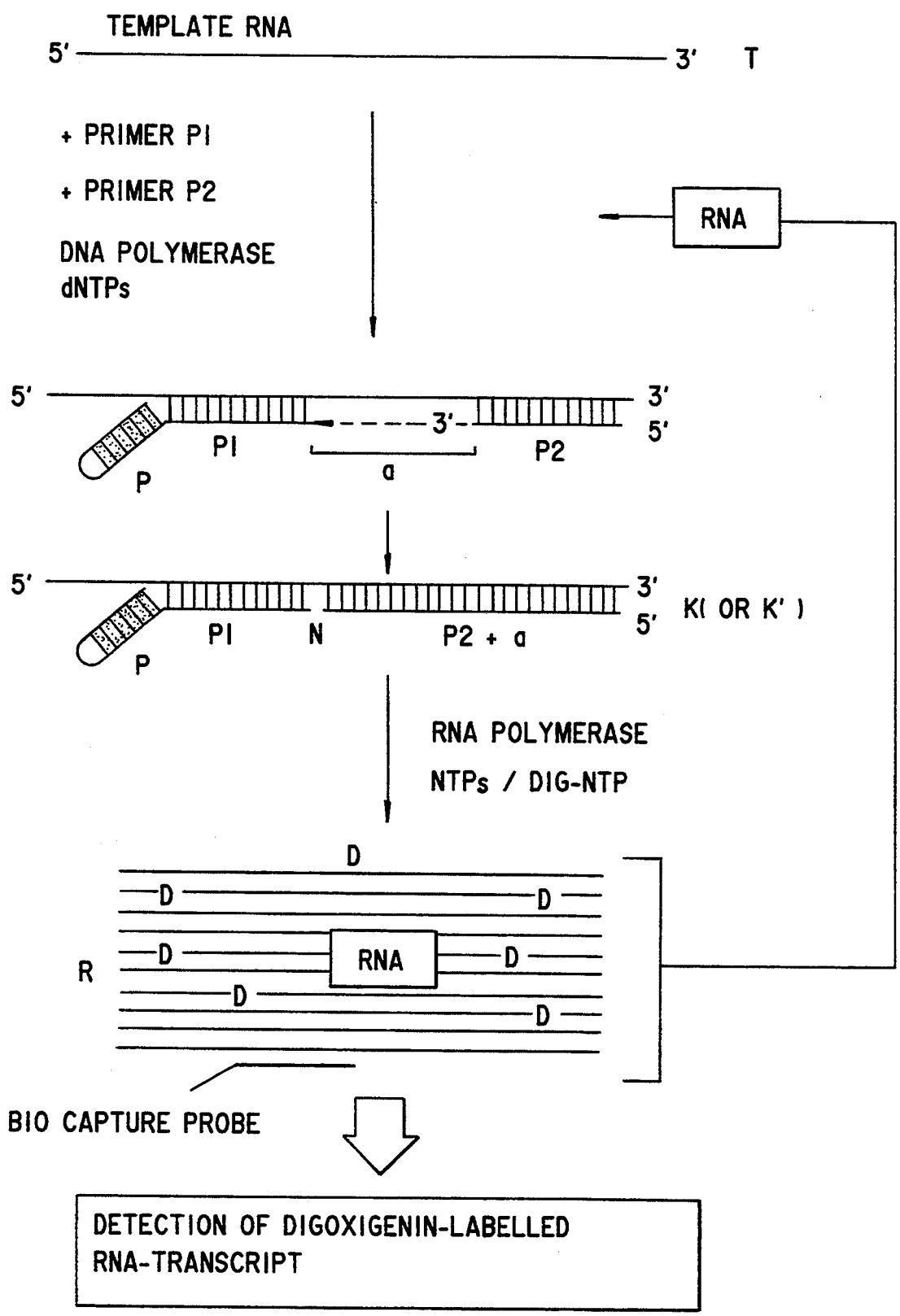

An embodiment is described in FIG. 4 in which, after formation of the nucleic acid complex K, a single-stranded region is firstly filled up between oligonucleotide P1 and oligonucleotide P2 by means of DNA polymerase before the transcription is carried out. The capture probe hybridizes preferably in the filled up region a.

FIG. 5 shows the relevant part of a template nucleic acid. It is the plasmid pSPT18neoxEco R1. The regions in which oligonucleotide P1 and oligonucleotide P2 can hybridize are indicated.

Figure 6:
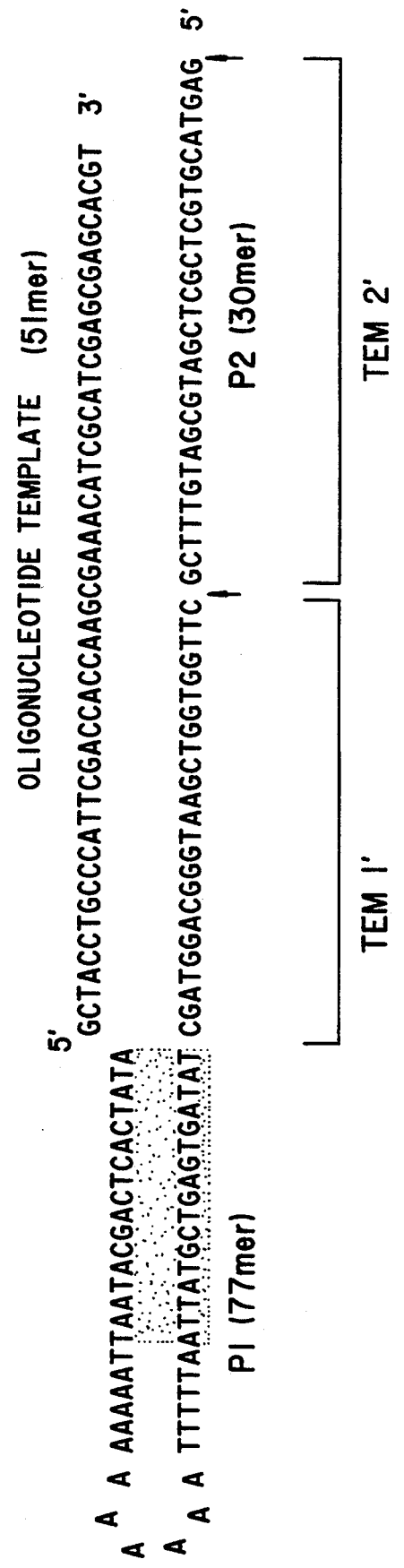

FIG. 6 shows how the nucleotide sequence of a chemically synthesized template, P1 and P2 can be arranged.

Figure 7:
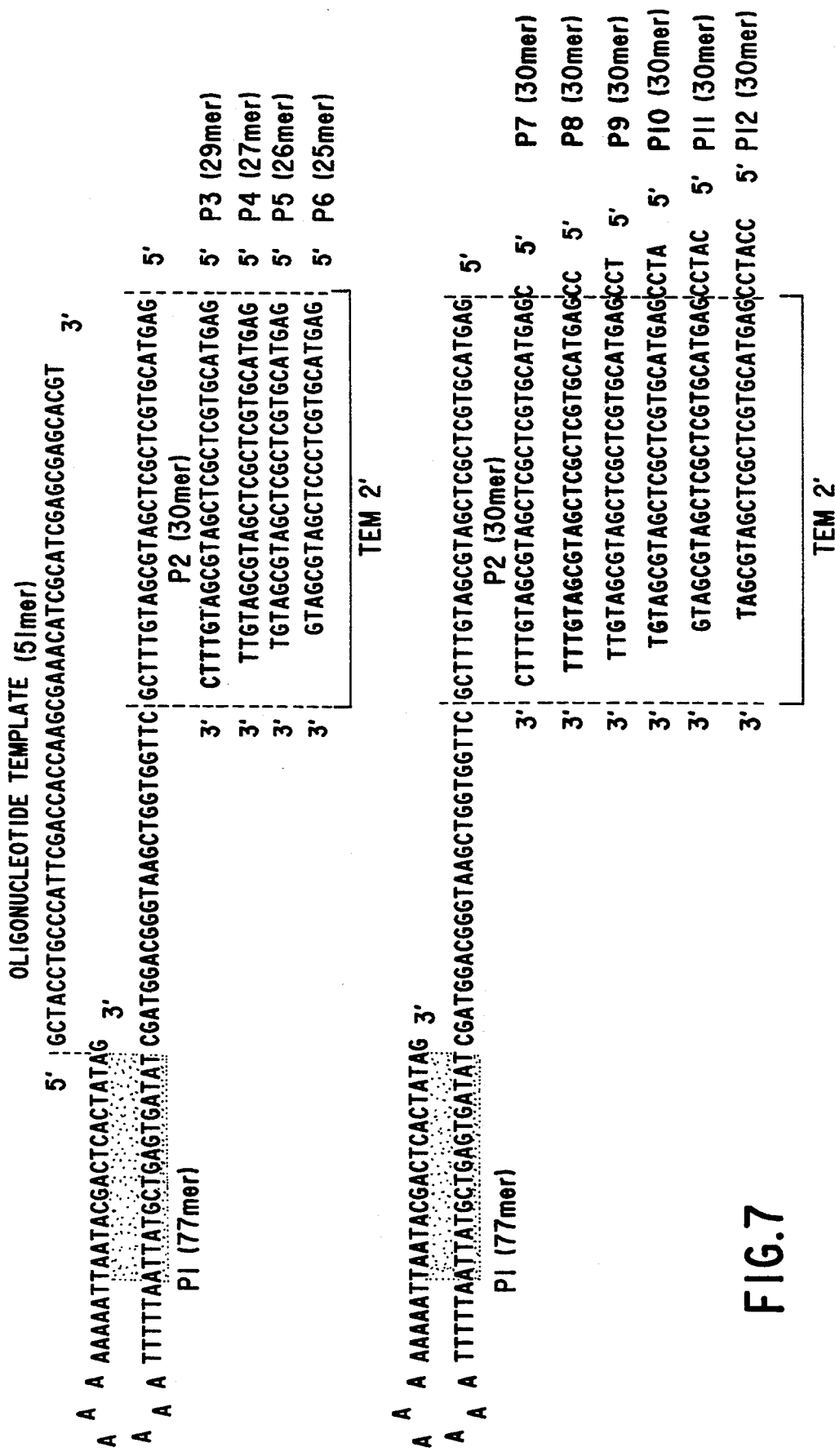

FIG. 7 shows how a set of oligonucleotides P3–P6 (or P7–P12) can serve to produce transcripts in which certain oligonucleotides are deleted compared to the template (by different lengths of the gap region between primer P1 and primer P2).

LIST OF ABBREVIATIONS

T template nucleic acid
K transcribable nucleic acid complex of P1, P2 and T
K' transcribable nucleic acid complex of P1, P2 and R
R transcript (RNA)
P1 template-specific promoter oligonucleotide
P2 template-specific oligonucleotide
P promoter region (double-stranded) (corresponds to PRO)
TEM 1 sequence on the template nucleic acid which is located nearest the transcription starting point
TEM 2 sequence on the template nucleic acid which is located farthest away from the transcription starting point
TEM 1' template-specific region of P1
TEM 2' template-specific region of P2
BIO biotin
BLO1' nucleotide region upstream of TEM 1
BLO2' nucleotide region downstream of TEM 2
BLO1 oligonucleotide complementary to BLO1'
BLO2 oligonucleotide complementary to BLO2'
D Digoxigenin
a filling up region
NTP ribonucleoside triphosphate
dNTP deoxyribonucleoside triphosphate
N nick in transcription unit The invention is elucidated in more detail by the following examples.

EXAMPLE 1

Production of RNA templates

Plasmid pSPT18 neo (sequence cf. WO 89/06698) is used for the production of transcripts of the neomycin resistance gene (neo). The neomycin gene (an aminoglycoside-3'-phosphotransferase II) is inserted into pSPT18 as described by Beck et. al. (1982), Gene, 19, 327-336. Transcripts of the gene in the sense orientation can be produced from the resulting plasmid pSPT18neo using SP6 RNA polymerase. Plasmid pSPT18neo is linearized with the restriction endonuclease EcoRI. RNA transcripts, 1028 nucleotides in length, are produced from this linearized plasmid by in vitro transcription as described in Biochemicals for Molecular Biology, Boehringer Mannheim (1990), page 158. Position 1 of the transcript marks the SP6 RNA polymerase transcription starting point or the first nucleotide of the transcript. After phenol extraction to remove enzymatic components and ethanol precipitation, the transcripts purified in this way can be used in the following examples as templates.

EXAMPLE 2

Transcription on P1 (promoter construct with loop structure)

a) Production of P1

P1 consists of a nucleic acid strand of 77 nt in which 25 nt at its 5' end are complementary to the ribonucleotide positions 430-454 of the RNA transcript described in example 1 or to nucleotide positions 1933-1957 of the sequence described by Beck et. al. (see above) which contains the neogene. In addition P1 contains the minimal necessary self-complementary sequence of the promoter for the RNA polymerase of the bacteriophage T7 (sequence cf. P1 in FIG. 6) (J. F. Milligan et. al. (1987), Nucl. Acids Res., Vol. 15, No. 21, 8783-8798). These self-complementary sequences are separated from one another by an AT rich region which promotes the formation of the partial double strand in solution. In addition P1 can contain additional transcribable self-complementary but not template-complementary sequences which promote the transcription as described by J. F. Milligan et. al. (1987), Nucl. Acids Res., 15, p. 8783-8798.

After synthesis in an automated DNA synthesizer the DNA oligonucleotide of 77 nucleotides corresponding to P1 is purified by electrophoresis in a 20% denaturing polyacrylamide gel as described in Molecular Cloning (1989), Editors Sambrook, Fritsch, Maniatis, CSH, pages 6.39-6.48. In order to enable an annealing of the self-complementary sequences of P1 which is as complete as possible, this DNA oligonucleotide is heated to 90° C. for 10 minutes in a reaction vessel after the purification and subsequently it is cooled on ice for 10 minutes. P1 is examined for its ability to produce RNA transcripts in the presence of T7 RNA polymerase under the experimental conditions described in the following.

b) Transcription reaction

The reaction mixture contains the following in a final volume of 25 μl:

40 mmol/l Tris-HCl (pH 8.0 at 37° C.), 6 mmol/l $MgCl_2$, 10 mmol/l NaCl, 10 mmol/l dithiothreitol (DTT), 2 mmol/l spermidine-HCl, 5 % (v/v) polyethylene glycol MW 6000, 0.01% (v/v) Triton X-100, 2 mmol/l each of ATP, UTP, GTP, CTP (pH 8.0 at 37° C.), 5 μCi [$^{32}$P]-CTP (400 Ci/mmol, Amersham), 500 nmol/l primer 1, 15 U/μl T7 RNA polymerase (Boehringer Mannheim), 1 U/μl RNAse inhibitor (Boehringer Mannheim).

The non-enzymatic materials used are treated before use with 0.01% diethylpyrocarbonate as described in Molecular Cloning (see above) pages 7.3-7.4.

The individual components are mixed in a reaction vessel of 100 μl volume and the preparation is incubated for one hour at 37° C.

c) Detection

Afterwards the reaction is stopped by addition of an equal volume of formamide stop buffer (95% formamide, 25 mM EDTA, 0.01% xylene cyanol, 0.01% bromophenol blue), heating for 3 minutes to 68° C. and cooling the reaction mixture on ice. An aliquot of the denatured reaction preparation is then applied to a 7 M urea, 12% polyacrylamide gel with a layer thickness of 0.8 mm. The gel electrophoresis is carried out according to U.K. Laemmli (1970), Nature, 277, p. 680-685. The gel is subsequently autoradiographed and the radioactive products are analyzed.

The reaction can also be stopped by addition of 10 mmol/l EDTA and 0.1% SDS. For the detection the transcription products are then separated in a 1.5% denaturing agarose gel as described in Molecular Cloning (see above), pages 7.43-7.45 and the reaction products are visualized by staining in an acridinium orange solution (5 μg/ml).

If no [$^{32}$P]-CTP is added to the reaction mixture, the specific reaction products can, after gel electrophoresis in polyacrylamide gels, be transferred to a nylon membrane by Northern blotting, immobilized by UV and detected by in-situ hybridization with complementary, radioactively or non-radioactively labelled (Biochemicals for Molecular Biology, see above, p. 112-115) DNA oligonucleotides. This type of hybridization is described by J. Meinkoth and G. Wahl (1984), Anal. Biochem., 138, p. 267-284 and in Nucleic Acid Hybridization (1985) Editors B. D. Hames and S. J. Higgins, IRL Press, Oxford, p. 139-159.

After separation from non-incorporated [$^{32}$P]-CTp by gel filtration on a Sephadex G-50 column, the reaction products can also be detected by concentrating by ethanol precipitation, dropwise application onto a nylon membrane, UV immobilization, exposure of an X-ray film to the dried membrane and measurement of the resulting blackening of the film.

By incorporation of non-radioactively labelled NTPs instead of [$^{32}$P]-CTP the products can be visualized directly in DOT, SLOT or Northern blot. The incorporation of digoxigenin-11-UTP or biotin-16-UTP (cf. WO 89/06698) can be used for the direct detection with anti-digoxigenin-AP conjugate or with streptavidin-AP conjugate.

The detection is facilitated by reaction of alkaline phosphatase with the corresponding substrate 5-bromo-4-chloro-3-indoyl phosphate (X-phosphate) and nitroblue tetrazolium salt (NBT), via the change in colour of the reaction solution as described in Biochemicals for Molecular Biology (see above) p. 109-115 or by a chemiluminescence reaction mediated by alkaline phosphatase using 3-(2'-spiroadamantan)4-methoxy4-(3''-phosphoryloxy)-phenyl-1,2-dioxetan (AMPPD, Boehringer Mannheim) as described by I. Bronstein and P. McGrath (1989), Nature, 338, p. 599-600.

The sensitivity of the chemiluminescence reaction can be increased further by addition of 5.6 μmol/l 5-N- tetradecanoylaminofluorescein (fluorescence enhancer) in 0.75 mol/l 2-amino-2-methyl-1-propanol buffer, pH 9.6 as described by M. Musani et. al. (1991) Anal. Biochem., 194, p. 394–398. The light emission caused by the chemiluminescence is documented by exposing a Polaroid or an X-ray film.

RNA is produced which extends from the transcription start on the promoter up to the 5' end of P1.

EXAMPLE 3

Transcription of the hybrid of P1, P2 and RNA template or oligonucleotide template a) Production of P2 and the oligonucleotide template The sequence of P2 (DNA oligonucleotide of 30 nucleotides; sequence cf. FIG. 6) is complementary to the ribonucleotide positions 456–485 of the RNA transcript described in example 1 or to the nucleotide positions 1958–1987 of the sequence described by Beck et. al. (see above) which contains the neogene. This complementary sequence is chosen so that the 3' end of primer 2 can hybridize with the RNA template directly adjacent to the 5' end of P1. The DNA oligonucleotide of 30 nucleotides corresponding to P2 is purified after the synthesis as described in example 2.

The sequence of the oligonucleotide template (DNA oligonucleotide of 51 nucleotides; sequence cf. FIG. 6) is homologous to the ribonucleotide positions 430–481 of the RNA transcript described in example 1. This homologous sequence to the RNA template is selected such that the template-complementary regions of P1 and P2 hybridize directly adjacent to one another on the oligonucleotide template.

b) Transcription reaction

In order to enable an annealing of the complementary sequences of P1 and P2 on the template nucleic acid which is as complete as possible, equimolar amounts of these DNA oligonucleotides and the template nucleic acid are heated to 90° C. for 10 minutes in a reaction vessel before addition of the other reaction components and cooled for 10 minutes on ice. Subsequently the denatured DNA oligonucleotides are incubated for 10 minutes at 37° C. in order to form the hairpin structure of P1. The transcription buffer and the enzymatic components (see example 2) are mixed in a reaction vessel and the preincubated oligonucleotides P1 and P2 are each added at a final concentration of 500 nmol/l. The reaction mixture is incubated for one hour at 37° C.

The transcription reaction is carried out as in example 2.

Subsequently the reaction products are detected as described in example 2 and the RNA products are analyzed.

RNA is produced which extends from the transcription start on the promoter within P1 up to the 5' end of P2.

EXAMPLE 4

Transcription of the hybrids of primer P1, one of the primers P2 to P6 and RNA template or oligonucleotide template.

a) Production of the primers 3–6 (single-stranded, linear)

The sequence of the primer P3 (DNA oligonucleotide of 29 nucleotides; sequence cf. FIG. 7) is complementary to the ribonucleotide positions 457–485 of the RNA transcript described in example 1 or to the nucleotide positions 1959–1987 of the sequence described by Beck et. al. (see above).

The sequence of the primer P4 (DNA oligonucleotide of 27 nucleotides; sequence cf. FIG. 7) is complementary to the ribonucleotide positions 459–485 of the RNA transcript described in example 1 or to the nucleotide positions 1961–1987 of the sequence described by Beck et. al. (see above).

The sequence of the primer P5 (DNA oligonucleotide of 26 nucleotides; sequence cf. FIG. 7) is complementary to the ribonucleotide positions 461–485 of the RNA transcript described in example 1 or to the nucleotide positions 1962–1987 of the sequence described by Beck et. al. (see above).

The sequence of the primer P6 (DNA oligonucleotide of 25 nucleotides; sequence cf. FIG. 7) is complementary to the ribonucleotide positions 461–485 of the RNA transcript described in example 1 or to the nucleotide positions 1963–1987 of the sequence described by Beck et. al. (see above).

These complementary sequences are chosen so that the 3' ends of the primers P3–P6 can hybridize with the RNA template not directly adjacent to the 5' end of the primer P1. The DNA oligonucleotides corresponding to the primers P3–P6 are purified after the synthesis as described in example 2.

The hybridization products of primer P1, primers P3–P6 and RNA template or oligonucleotide template are tested for the ability of T7 RNA polymerase to read through the "gaps" formed between primer P1 and primers P3–P6 in the coding nucleic acid strand during transcription.

b) Transcription reaction

The transcription reaction is carried out as in example 2.

In order to enable an annealing of the complementary sequences of the primers P1 and P3–P6 to the template nucleic acid which is as complete as possible, equimolar amounts of these DNA oligonucleotides are heated to 90° C. for 10 minutes in a reaction vessel before addition of the other reaction components and cooled for 10 minutes on ice. Subsequently the denatured DNA oligonucleotides are hybridized for 10 minutes at 37° C.

The transcription buffer and the enzymatic components (see example 2) are mixed in a reaction vessel and the oligonucleotides P1 and P3–P6 are each added at a final concentration of 500 nmol/l. The reaction preparation is incubated for one hour at 37° C.

Subsequently the reaction products are detected as described in example 2 and the RNA products are analyzed.

RNA is produced which extends from the transcription start on the promoter within the primer P1 up to the 5' end of the primers P3–P6. The length of the transcripts which are produced is 54 nt (for primer P3), 52 nt (for primer P4), 51 nt (for primer P5) and 50 nt for primer P6 in the preparation.

The missing nucleotides in the "gap" region are read through and RNA transcripts are produced which have the length of the double-stranded region in the transcribable complex K.

EXAMPLE 5

Transcription of the hybrids from primers P1, P7 to P12 and RNA template or oligonucleotide template.

a) Production of the primers P7–P12 (single-stranded, linear)

The sequence of the primer P7 (DNA oligonucleotide of 30 nucleotides; sequence cf. FIG. 7) is complementary to the ribonucleotide positions 457–486 of the RNA transcript described in example 1 or to the nucleotide positions 1959–1988 of the sequence described by Beck et. al. (see above).

The sequence of the primer P8 (DNA oligonucleotide of 30 nucleotides; sequence cf. FIG. 7) is complementary to the ribonucleotide positions 458–487 of the RNA transcript described in example 1 or to the nucleotide positions 1960–1989 of the sequence described by Beck et. al. (see above).

The sequence of the primer P9 (DNA oligonucleotide of 30 nucleotides; sequence cf. FIG. 7) is complementary to the ribonucleotide positions 459–488 of the RNA transcript described in example 1 or to the nucleotide positions 1961–1990 of the sequence described by Beck et. al. (see above).

The sequence of the primer P10 (DNA oligonucleotide of 30 nucleotides; sequence cf. FIG. 7) is complementary to the ribonucleotide positions 460–489 of the RNA transcript described in example 1 or to the nucleotide positions 1962–1991 of the sequence described by Beck et. al. (see above).

The sequence of the primer P11 (DNA oligonucleotide of 30 nucleotides; sequence cf. FIG. 7) is complementary to the ribonucleotide positions 461–490 of the RNA transcript described in example 1 or to the nucleotide positions 1963–1992 of the sequence described by Beck et. al. (see above).

The sequence of the primer P12 (DNA oligonucleotide of 30 nucleotides; sequence cf. FIG. 7) is complementary to the ribonucleotide positions 462–491 of the RNA transcript described in example 1 or to the nucleotide positions 1964–1993 of the sequence described by Beck et. al. (see above).

These complementary sequences are so chosen that the 3' ends of the primers P7–P12 can hybridize with the RNA template not directly adjacent to the 5' end of the primer P1. The DNA oligonucleotides corresponding to the primers P7–P12 are purified after the synthesis as described in example 2.

The hybridization products of primer P1, primers P7–P12 and RNA template or oligonucleotide template are tested for the ability of T7 RNA polymerase to read through the "gaps" formed between primer P1 and primers P7–P12 in the coding nucleic acid strand during the transcription and to produce RNA transcripts which have the length of the double-stranded region in the transcribable complex K.

b) Transcription reaction

The transcription reaction is carried out as in example 2.

In order to enable an annealing of the complementary sequences of the primers P1 and P7–P12 to the template nucleic acid which is as complete as possible, equimolar amounts of these DNA oligonucleotides together with the template nucleic acid are heated to 90° C. for 10 minutes in a reaction vessel before addition of the other reaction components and cooled for 10 minutes on ice. Subsequently the DNA oligonucleotides are incubated for 10 minutes at 37° C.

The transcription buffer and the enzymatic components (see example 2) are mixed in a reaction vessel and the oligonucleotides primer 1 and primers 7–12 are each added at a final concentration of 500 nmol/l. The reaction mixture is incubated for one hour at 37° C.

Subsequently the reaction products are detected as described in example 2 and the RNA products are analyzed.

RNA is produced which extends from the transcription start on the promoter within the primer 1 up to the 5' end of the primers 7–12. The length of the transcripts which are produced is 55 nt in all the preparations (with the primers 7–12).

The missing nucleotides in the region of the single gap are read through and the transcription does not stop or initiate in this region.

EXAMPLE 6

Range of variation of the reaction

Reaction conditions are given in the following within which the process according to the present invention can be carried out successfully. Using this a person skilled in the art can, however, also determine conditions which differ from this on the basis of a few experiments.

|  | Optimal conditions | Range of variation |
| --- | --- | --- |
| Tris-HCl | 40 mM (pH 8.0) | 2–150 mM (pH 7.5–8.5) |
| MgCl$_2$ | 6 mM | 2–20 mM |
| NaCl | 10 mM | 0–200 mM |
| DTT | 10 mM | 2–20 mM |
| Spermidine-HCl | 2 mM | 0–10 mM |
| PEG 6000 | 5% | 2–10% |
| Triton X-100 | 0.01% | 0.01–0.5% |
| BSA | — | 0–100 g/ml |
| RNAase inhibitor | 1 U/µl | 0–5 U/µl |
| NTPs | 2 mM | 0.2–5 mM |
| Primer 1/2/3 | 500 nM | 100 nM–1.5 µM |
| Primer 4/5 | — | 0–1.5 µmol |
| RNA polymerases | T7 RNA polymerase | T7, SP6, T3 RNA, N4 polymerases |
| T7 RNA polymerase | 15 U/µl | 5–25 U/µl |
| Reaction temp. | 37° C. | 35–42° C. |
| Reaction time | 60 min | 20 min–3 hours |
| Reaction volume | 25 µl | 20–200 µl |
| Prehybridization | 0–30 min. | 0–6 h |

We claim:

1. A process for the specific production of ribonucleic acids comprising the steps of:
    a) hybridizing a template specific promotor oligonucleotide P1 and a template specific oligonucleotide P2 with a template nucleic acid T to form a complex K, and
    b) forming transcripts R containing at least the template specific sequence information from P1 to P2 by promotor controlled transcription,
wherein the oligonucleotides P1 and P2 used are not enzymatically ligated together in any step in the process.

2. The process according to claim 1, further comprising the steps of:
    hybridizing the transcripts R with oligonucleotides P1 and P2 to form complex K', and
    transcribing K' by promotor controlled transcription.

3. The process according to claim 1, wherein the amount of P1 is equal to the amount of P2.

4. The process according to claim 1, wherein the process is carried out at one temperature.

5. The process according to claim 1, wherein monoribonucleoside triphosphates which are detectably labelled or capable of being immobilized are incorporated into the transcripts R during transcription.

6. The process according to claim 1, wherein P2 is immobilized or capable of being immobilized.

7. The process according to claim 1, wherein the transcripts R formed in step b) contain at least the template specific information from P1 to P2.

8. A process for the specific detection of a template nucleic acid comprising the steps of:
    a) hybridizing a template specific promotor oligonucleotide P1 and a template specific oligonucleotide P2 with a template nucleic acid T to form a complex K,
    b) forming transcripts R containing at least the template specific sequence information from P1 to P2 by promotor controlled transcription, and
    c) detecting said transcripts R, wherein the oligonucleotides P1 and P2 used are not enzymatically ligated together in any step in the process.

9. The process according to claim 8, further comprising the steps of:
    hybridizing the transcripts R with oligonucleotides P1 and P2 to form complex K', and
    transcribing K' by promotor controlled transcription.

10. The process according to claim 8, wherein monoribonucleoside triphosphates which are detectably labeled or capable of being immobilized are incorporated into the transcripts R during transcription.

11. The process according to claim 8, wherein P2 is immobilized or capable of being immobilized.

* * * * *